United States Patent [19]
Sautter et al.

[11] Patent Number: 5,976,880
[45] Date of Patent: Nov. 2, 1999

[54] PROCESS AND APPARATUS FOR THE GENETIC TRANSFORMATION OF CELLS

[75] Inventors: Christof Sautter, Rafz; Heinz Waldner, Zurich; Ingo Potrykus, Magden, all of Switzerland

[73] Assignee: Novartis Finance Corporation, New York, N.Y.

[21] Appl. No.: 07/629,689

[22] Filed: Dec. 18, 1990

[30] Foreign Application Priority Data

Dec. 19, 1989 [CH] Switzerland .............................. 4562/89

[51] Int. Cl.$^6$ .............................. C12N 1/20; C12N 13/00
[52] U.S. Cl. .......................... 435/470; 435/471; 435/468; 435/252.3; 435/173.6
[58] Field of Search ............................. 435/172.1, 172.3; 604/70; 935/85

[56] References Cited

U.S. PATENT DOCUMENTS

| | | | |
|---|---|---|---|
| 4,945,050 | 7/1990 | Sanford et al. | 435/172.1 |
| 5,141,131 | 8/1992 | Miller et al. | 222/54 |
| 5,240,842 | 8/1993 | Mets | 435/172.3 |

FOREIGN PATENT DOCUMENTS

| | | |
|---|---|---|
| 0 270356 | 6/1988 | European Pat. Off. . |
| 0 301749 | 2/1989 | European Pat. Off. . |
| 91/00915 | 1/1991 | WIPO . |

OTHER PUBLICATIONS

"The Biolistic Process", Trends in Biotechnology, John Sandford, vol. 6, Dec. 1988, pp. 299–302.
"Factors Influencing Gene Delivery Into Zea Mays Cells By High–Velocity Microprojectiles", Bio/Technology, T.M. Klein et al, vol. 6 May 1988 pp. 559–563.
"Transfer Of Foreign Genes Into Intact Maize Cells With High–Velocity Microprojectiles", Proc. Natl. Acad. Sci., Theodore Klein et al, vol. 85, pp. 4305–4309, Jun. 1988.
"Mitochondrial Transformation In Yeast By Bombardment With Microprojectiles", Science, vol. 240, Stephen Johnston et al, pp. 1538–1541, Jun. 1988.
"High–Velocity Microprojectiles For Delivering Nucleic Acids Into Living Cells", May 7, 1987 Nature, Klein et al vol. 327, pp. 70–73.
"The Biolistic Process" Dec. 1988 Trends in Biotechnology, John Sandford, vol. 6, pp. 299–302.
"Factors Influencing Gene Delivery Into Zea Mays Cells By High–Velocity Microprojectiles" May 1988 Bio/Technology, T.M. Klein et al, vol. 6, pp. 559–563.

"Inheritance And Expression Of Foreign Genes In Transgenic Soybean Plants", Oct. 1989 Proceedings of the National Academy of Sciences in the USA, Paul Christou et al, vol. 86 No. 19, pp. 7500–7504.
"Transfer Of Foreign Genes Into Intact Maize Cells With High–Velocity Microprojectiles", Jun. 1988 Proc. Natl. Acad. Sci., Theodore Klein et al, vol. 85, pp. 4305–4309.
"Mitochondrial Transformation In Yeast By Bombardment With Microprojectiles", Jun. 1988 Science, Stephen Johnston et al, vol. 240, pp. 1538–1541.
"Transient Expression Of Foreign Genes In Rice, Wheat And Soybean Cells Following Particle Bombardment", 1988 Plant Molecular Biology, Yi–Chang Wang et al, vol. 11 pp. 433–439.
"Stable Transformation Of Soybean Callus By DNA–Coated Gold Particles" 1988 Plant Physiol Christian et al, vol. 87 pp. 671–674.
"Delivery of Substances Into cells And Tissue Using A Particle Bombardment Process", 1987 Particulate Science and Technology, John Sanford et al, vol. 5, pp. 27–37.
"Shooting Genes Into Plant Cells", Jul. 1987 TibTech, Bryant, vol. 5, p. 181.
"DNA Delivery By Microprojectiles Accelerated By a 'Vaccination Gun'" Apr. 1989 Miller et al, Journal of Cellular Biochemistry, vol. 13D, pp. 264. Abstract M 138.
"Chloroplast Transformation In Chlamydomonas With High Velocity Microprojectiles", Jun. 1998 Science, John Boynton et al, vol. 240, pp. 1534–1538.
"Stable Transformation Of Soybean (Glycine Max) By Particle Acceleration", Aug. 1988, Bio/Technology, Dennis E. McCabe et al, vol. 6, pp. 923–926.
"Transient Gene Expression in Maize, Rice, and Wheat Cells Using An Airgun Apparatus" 1990, Plant Physiol, James H. Oard et al, vol. 92 pp. 334–339.
Israel et al 1967 J of Colloid and Interface Science 24: 330–337.

*Primary Examiner*—Lynette R. F. Smith
*Attorney, Agent, or Firm*—Larry W. Stults

[57] ABSTRACT

In a tubular pressure chamber a drop of a DNA solution with gold particles suspended therein is atomized at the opening of a cannula by a pressure impact. The fog droplets containing the gold particles and the DNA entrained by them, are pressured by the pressure impact through a restriction at the end of the pressure chamber and thereby accelerated and focused. They subsequently traverse in free flight an evacuated specimen chamber and impact in a narrowly limited target area with a predetermined pulse, cells fixed on a holder, thereby penetrating them.

16 Claims, 2 Drawing Sheets

Fig. 1

PROCESS AND APPARATUS FOR THE GENETIC TRANSFORMATION OF CELLS

BACKGROUND OF THE INVENTION

The invention concerns a process for the genetic transformation of cells, in particular plant cells, together with an apparatus to carry out the process for the insertion of particles in cells. Such a process and a corresponding apparatus are described for example in EP-A-0 270 356.

The present invention further concerns the application of the process according to the invention to the preparation of transgenic plants, together with transgenic plants obtainable by said process and the progeny thereof.

Numerous processes and methods are available at the present time for the genetic manipulation of the genotype of plants by means of the recombinant DNA technology; they are routinely used in many laboratories.

The most effectively investigated and most frequently used processes undoubtedly include the Agrobacterium transformation system.

Agrobacterium cells have on their Ti-plasmid a large DNA fragment, the so-called T-DNA region, which in the natural transformation of plant cells is integrated into the plant genome.

This natural gene transfer system may be used after carrying out different modifications as a gene vector system for the controlled transformation of plants (Chilton, Md., 1983).

However, the Agrobacterium transformation system has the decisive disadvantage that the effective range of Agrobacteria is restricted to certain dicotyledonous plants and a few representative of the monocotyledons (Hernalsteens & al., 1984; Hookas-Van-Slogteren & al, 1984), which are insignificant from an agricultural economic standpoint. This signifies that the most important cultivated plants are not accessible for effective gene transfer.

Furthermore, the agrobacteria used are pathogens, which in their host plants induce characteristic disease symptoms in the form of cancer like tissue growths and which therefore may be handled under strict safety regulations in the laboratory only.

Alternative transformation systems, which were developed to equalize the disadvantages of the Agrobacterium transformation systems and which are directed at the transfer of exogenic DNA into plant protoplasts, such as the direct gene transfer of DNA in protoplasts (Paszkowski & al., 1984, Potrykus & al., 1986) and the microinjection of vector-free DNA in protoplasts (Steinbiss and Stabel, 1983; Morikawa and Yamada, 1985) or cells (Nomura and Komamime, 1986), must be considered problematic to the extent that the regeneration of entire plants from plant protoplasts of a plurality of plant species, in particular from the group of the gramineae still poses numerous problems at the present time.

Another disadvantage of these alternative transformation systems concerns as before, the relatively low transformation rates, which at this time have values of 1 to 5%.

These low transformation rates make it necessary to provide the DNA to be inserted with markers (for example antibiotics resistance genes), which make possible the rapid selection of the transformants from the large number of untransformed cells.

This means, however, that at the present time no satisfactory transformation process is available, which permits even the commercially efficient and cost efficient production of transgenic plants with novel and useful properties, in particular with regard to plants of the group of monocotyledoneae.

It is therefore an urgent task to develop processes making possible the rapid, efficient and reproducible transformation of all plants independently of their taxonomic position and the peculiarities resulting from it, thereby assuring the effective and economic production of transgenic plants, even commercially.

This is especially true relative to plants of the group of the monocotyledoneae, particularly those of the family of the gramineae, which includes the economically most important cultivated plants, such as wheat, barley, rye, oats, corn, rice, millet and the like, and which therefore are of a very special economic interest, particularly as no satisfactory process is available at this time for the preparation of transgenic monocotyledonous plants. Initial attempts in this direction consist of different, very recently developed transformation processes based on the insertion of DNA into plant cells included in a higher organized unit, such as for example an intact tissue body, an embryo or a whole, completely developed plant. This involves on the one hand the injection of exogenic DNA into the young inflorescence of rye plants (de la Pena & al., 1987), and on the other, a virus infection of corn plants, transmitted by Agrobacterium, with "maize streak virus" (Grimsley & al., 1987). However, these newly developed processes also have their disadvantages; thus for example, the process first mentioned above has not been reproducible to date.

An alternative process, again involving the transformation of plant cells within a higher organized unit, is based on the bombardment of said cells with particles associated with the DNA to be transformed. The impact of these highly accelerated particles produces holes in the cell walls of the cells impacted, through which the particles enter the cell, together with their associated DNA.

By means of these so-called microprojectiles a multitude of cells may be reached very rapidly. Microprojectiles have already been used in the past for gene transfer (Klein & al., 1988; Christou & al., 1988; EP-A-0 270 356) and were found to be suitable relative to certain problem definitions. However, the commercially available ballistic devices are not particularly suitable for the bombardment of small tissue areas with correspondingly small cells, such as for example in the case of the meristems. As the metal particles are fired dry in the ballistic processes, aggregates of a few or of many particles are fired which almost always tear deep wounds in the specimen. This tendency to aggregate is further enhanced by the bonding of the DNA on the particles.

The generally very high particle velocity of the ballistic processes requires a large working distance, which leads to the strong scattering of the particles. The particle velocity can be affected in the known ballistic methods in large stages only. It is hardly possible in this manner to improve the strong scattering of the particles. However, small tissues with small cells require dense coverage of the specimen with uniformly distributed individual particles in a narrowly limited target field, in order to obtain high transformation rates. The pulse of the particles should be as similar as possible, i.e. it should be possible to control the velocity and mass, the particle density on the specimen and the particle velocity very finely, so as to be able to adapt to different tissues.

SUMMARY OF THE INVENTION

These requirements are satisfied by the process of the invention and by the apparatus according to the invention.

Advantageous embodiments and further developments are also described.

According to the process of the invention, microprojectiles in the form of particles, in particular gold particles, of a highly defined size are atomized in suspension with a DNA solution by a pressure impact, into a fine fog. The droplets of the fog contain the particles and the DNA and are only slightly larger than the particles themselves. The fog is pressured by the same pressure impact through fine pores or capillaries and thereby accelerated. Upon impact on the cells, the particles produce holes in the cell walls and the plasma membranes, through which the DNA entrained in the fog droplets is able to enter the cells. On a target surface of less than 1 mm in diameter, the particle density and the velocity of the particles can be finely controlled within wide limits. The process according to the invention can be produced in a technically very simple and cost effective manner and can operate very reliably.

Particularly suitable and therefore preferred for the application of the transformation process according to the invention are tissue formations with few cells, in particular meristematic tissue formations, such as those present for example in the shoot meristema of plants, in proembryos and embryos or in embryogenic cell cultures.

BRIEF DESCRIPTION OF THE DRAWINGS

Other objects and advantages of the present invention will become more apparent from the following detailed description of preferred embodiments as described with reference to the drawings in which:

FIG. 2 shows a longitudinal section through essential parts of an apparatus at an enlarged scale; and, FIG. 3 shows a section on the line III—III of FIG. 2.

DETAILED DESCRIPTION OF THE PREFERRED EMBODIMENTS

As seen in the drawing, the apparatus of the invention comprises a longitudinal, essentially cylindrical pressure chamber 1, a subsequent specimen chamber 2, a device 3 for the generation of a pressure impact in the pressure chamber and a suction device to be connected with the specimen chamber, for example in the form of a water jet vacuum pump 5.

The apparatus 3 to generate a pressure impact comprises a $CO_2$ gun 31 attached to the rear end (not shown), together with a $CO_2$ supply cylinder 32. In place of a $CO_2$ gun, a compressed air cylinder may also be provided. Furthermore, the $CO_2$ gun may be operated with cartridges, whereby the cylinder 32 may be eliminated. It is merely essential that the apparatus be capable of generating highly uniform pressure impacts of a predetermined magnitude in the pressure chamber within a range of a few bars to approximately several hundred bars, or possibly higher. Further, it should preferably be possible to produce a plurality of pressure impacts in succession with a relatively high repetition frequency (about 1 discharge/s).

Figures 2, 3:
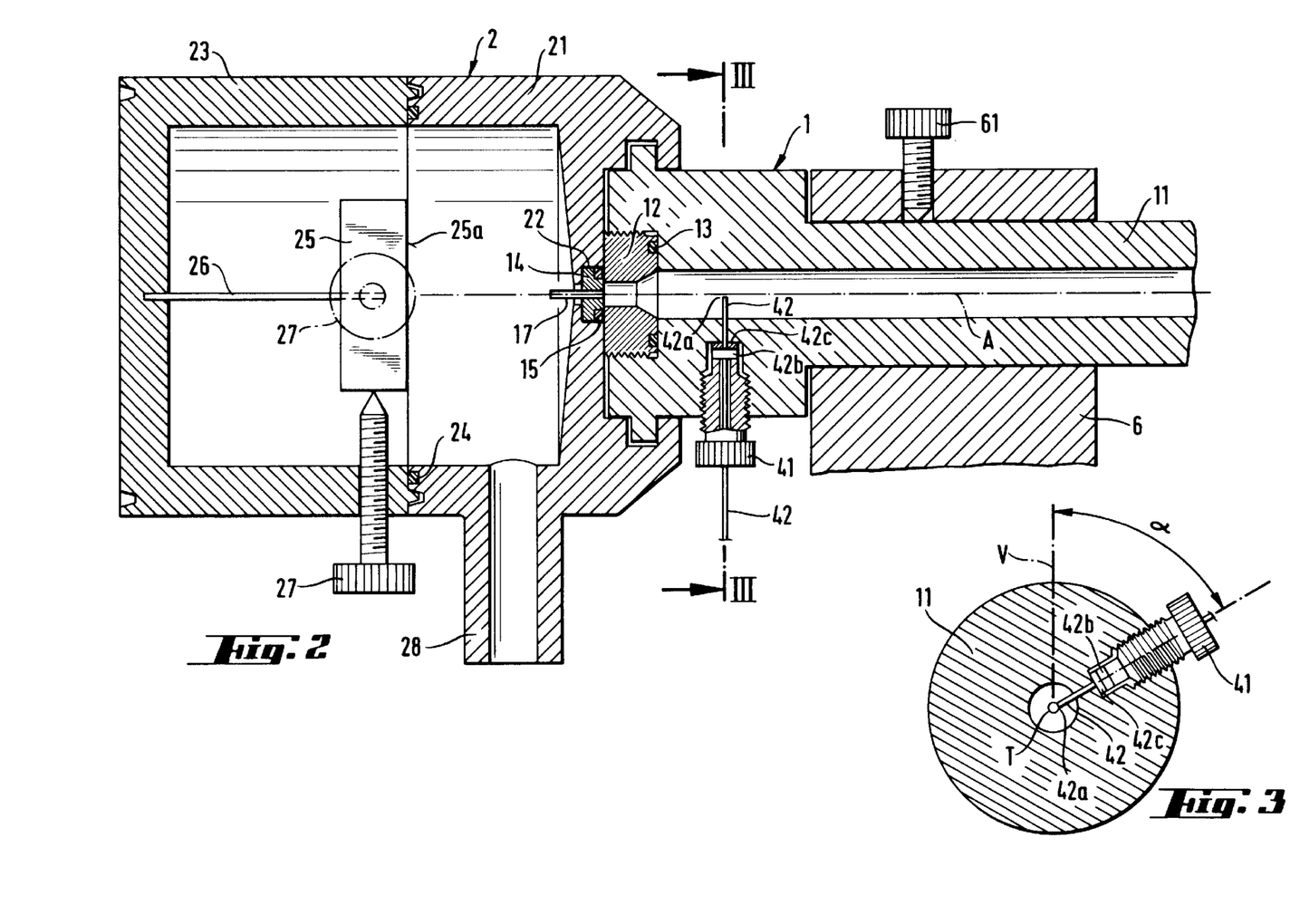

The configuration of the pressure chamber 1 is shown in detail in FIG. 2. It consists essentially of a relatively thick-walled, pressure resistant steel tube 11 with a length of about 50 mm and an internal diameter of about 3 mm, clamped into a stationary support block 6 in an approximately horizontal position and capable of rotation around its longitudinal axis A. A locking screw 61 immobilizes the tube 11 in its prevailing position.

At the rear end of the steel tube 11, to the right in the drawing, the muzzle of the $CO_2$ gun 31 is attached directly, in an appropriate manner (not shown). A taper ring 12 is set into the front end of the tube 11 and sealed with an O ring. The taper ring reduces the internal diameter of the steel tube conically in the direction of its end, by about one-half.

To the front end of the steel tube 11 or pressure chamber, an essentially cup shaped base part 21 of the specimen chamber 2, which as a whole is essentially cylindrical, is attached by means of a bayonet lock or the like, in a sealed and releasable manner. The base part 21 is provided with a cylindrical recess 22 to retain a capillary holder 14, by pressing it with the insertion of another O ring 15, which seals against the outer frontal surface of the taper ring 12. A capillary 17 is sealed into the capillary holder 14 exactly flush with the longitudinal axis A of the pressure chamber. The capillary 17 thus connects the internal space of the pressure chamber 1 with the internal space of the specimen chamber 2. In other words, the pressure chamber 1 opens into a restriction formed by the capillary 17. In place of the capillary 17, a restriction in the form of a flow diaphragm or generally a pore, may also be provided.

The specimen chamber 2 consists of the aforementioned base part 21 resealably mounted on the steel tube 11, and another, again essentially cup shaped wall part 23, attached releasably to the base part 21, with another O ring 24 sealing off the two parts. In the wall part 23, which may be removed from the base part 21, a plate shaped cell holder 25 is located, mounted on an elastic support arm 25, made of spring steel. Its flat frontal surface 25a, serving to hold the cells to be bombarded in place, is placed essentially perpendicular to the longitudinal axis A of the pressure chamber 1. The cell holder 25 may be displaced by means of two adjusting screws 27, located in the removable wall part 23 of the specimen chamber 2, in two perpendicular directions transverse to the longitudinal axis A of the pressure chamber 1 and therefore adjusted relative to the restriction or capillary 17. The second adjusting screw is perpendicular to the plane of the drawing. The base part 21 of the specimen chamber 2 attached to the steel tube 11, is equipped with a connector fitting 28 for the water jet vacuum pump 5 or another suitable suction or evacuating device. The connection of the base part 21 and the removable wall part 23 is essentially without clearance, so that the position of the cell holder 25 relative to the restriction 17 cannot vary when the wall part 23 is removed and replaced.

Figure 1:
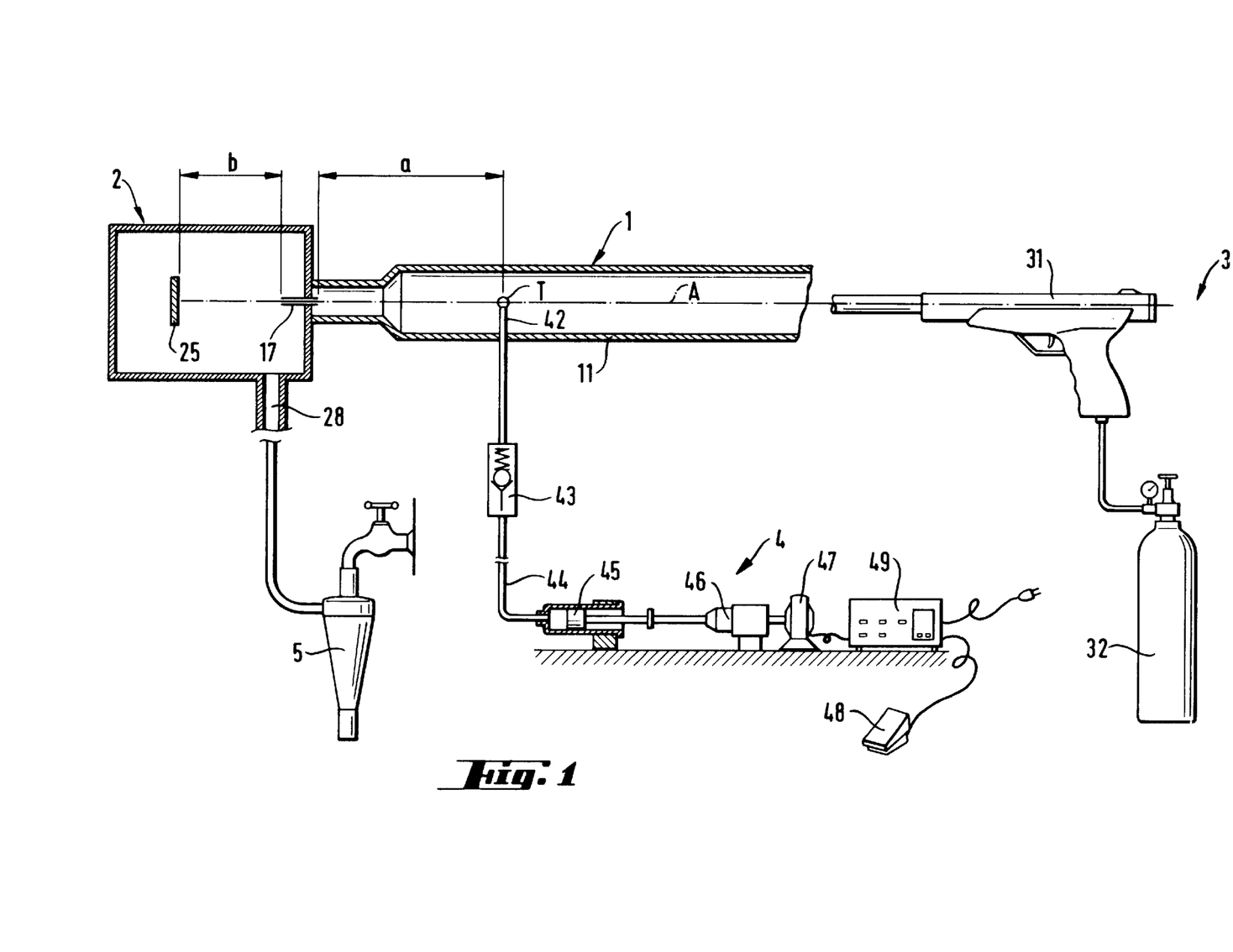
FIG. 1 shows a fundamental diagram of an exemplary embodiment of the process according to the invention.

In the front part of the pressure chamber 1, into the jacket of the steel tube 1, a hollow nipple 41 is screwed, through which a steel cannula 42 is inserted radially into the steel tube 11. To secure and seal the steel cannula (external diameter about 0.75 mm, internal diameter about 0.5 mm) a metal bead 42b formed on the cannula and a PTFE (teflon) gasket 44c are provided. The opening 42a of the steel cannula 42 is located tightly in front of the longitudinal axis A of the pressure chamber 1, so that a liquid droplet T exiting from the cannula 42 (FIG. 1) is located exactly in the longitudinal axis A.

For purposes of representation, the hollow nipple 41 and the steel cannula 42 are shown in FIG. 2 to open vertically from below into the steel tube 11. However, in actual operation the cannula 42 opens obliquely from above at an angle α to the vertical V into the pressure chamber 1, as shown in FIG. 3. The angle α may be adjusted as needed by rotating the steel tube 11 in the support block 6 (fixation by the fastening screw 61).

The steel cannula 42 is connected by means of a cheek valve 43 and a flexible line 44 with a metering aggregate, which consists of a metering syringe 45, a spindle drive (micrometer screw) 46, a step motor 47 and an electric control device 49 actuated by a foot switch 48. The metering aggregate, which in itself is conventional and thus requires no further explanation, is capable of feeding in a reproducible manner and within wide, adjustable limits, liquid volumes (suspension) in the microliter range through the cannula 42 into the pressure chamber 1, with the liquid (suspension) exiting from the cannula opening 42a in droplets.

The general operating mode of the apparatus is as follows:

The cells to be bombarded are fastened with the wall part 23 of the specimen chamber 2 removed in a manner explained below, to the surface 25a of the cell holder 25. The wall part 23 is then set onto the base part 21 and the specimen chamber 2 evacuated by means of the water jet pump 5. Subsequently, the metering apparatus 4 loaded with a DNA solution and the microprojectiles suspended therein in the form of very fine gold particles is activated, whereby at the opening 42a of the cannula 42 a suspension droplet T of the appropriate size (see the following detailed explanation) is produced. The $CO_2$ gun is then actuated and a pressure impact of a predetermined magnitude propagating essentially in the longitudinal direction A of the chamber, produced. This pressure impact atomizes the suspension droplet T present at the cannula opening 42a into a fine fog containing the gold particles and the DNA adhering to it. The gold particles thus entrain the DNA from the liquid phase and take them with them. The fine fog is now pressured by the pressure impact through the restriction formed by the capillary 17 and is thereby considerably accelerated. The fog droplets exiting from the capillary 17 containing the gold particles with the DNA adhering to them, now impact the cells fixed on the cell holder 25 within a very small scatter cone at a high velocity and penetrate them. With a suitable dimensioning of the apparatus and of the process parameters, it may always be obtained that only one particle and at the most only a few particles penetrate the cells and actually remain in them. The apparatus also assures an extremely high target accuracy (low scatter effect).

The specimen chamber 2 is (partially) evacuated. This reduces the friction of the fog droplets moving from the restriction 17 to the cell holder 25. Further, the droplet size is minimized and the directional scatter reduced. In addition, the (partial) vacuum stresses the cell walls, so that they may be better penetrated by the impacting particles. Conventional water jet pump vacuums (about 500 mm Hg) are normally adequate, while for special applications (for example in the case of more resistant cell walls) a higher vacuum (reduced pressure) is possible.

As mentioned above, the cannula 42 terminates tightly in front of the longitudinal axis A of the pressure chamber 1, so that the suspension droplet produced at the opening of the cannula opening is located exactly in the longitudinal axis A. In this manner, a droplet cloud symmetrical relative to the longitudinal axis, which again affects the target accuracy and the distribution of the particles in the impact area favorably is produced.

The distance a (FIG. 1) between the opening 42*a* of the cannula 42 and the inlet opening of the capillary 17 or the diaphragm of the pore is relatively critical. If this distance is too small, not a fog, i.e. individual fog droplets, are pressed through the restriction, but a closed liquid filament is passed from the restriction into the specimen chamber. Such a jet leads to massive destruction of the cells to be bombarded and must be avoided under all circumstances. In actual practice, this distance a must therefore amount to at least 5–10 mm, with this minimum value also depending on the dimensions of the other parts of the apparatus and is therefore to be determined empirically in all cases. The working distance b (FIG. 1) between the outlet end of the capillary 17 or the restriction in general, and the cell holder 25, i.e. the distance covered by the fog droplets in free flight in the vacuum, is less critical. Practical values are 5 mm to 5 cm, depending on the type of tissue and the nature of the restriction. The working distance affects, by means of the friction, (reduced by the partial vacuum) the particle velocity and through the scatter, the effective diameter of the target area. A value of approximately 10 mm has been found to be favorable.

As mentioned above, both a capillary or a flow diaphragm, or generally a pore may be used as the restriction. As the diaphragm, for example one made of platinumiridium, such as those used in electron microscopy, may be employed. The opening diameter of the diaphragms may be for example from 20 to 500 micrometers or even up to a 1 mm. Diameters of approximately 70–300 micrometers are preferred. Capillaries may consist of glass or a metal (for example steel). The values of the internal diameter are those cited for diaphragms. The capillaries may be 0.1–20 mm long, preferred values are within a range of 1.0–10 mm. The ratio of the internal diameter to the length of the capillaries determines the flow resistance. Longer capillaries therefore usually require larger internal diameters. The longer the capillary, the greater the acceleration path for the fog particles and the larger their terminal velocity upon their entrance into the specimen chamber will be.

The angle $\alpha$, at which the cannula 42 is inclined relative to the vertical V upon its opening into the pressure chamber 1 (FIG. 3), may be adjusted by the rotation of the tube 1 in the support block 6. As the gold particles with dimensions of about 1.2 um to 1.5 um are suspended in the DNA solution sediment without agitation, the angle is adjusted preferably in a manner such that with each metered volume essentially the same number of gold particles exits in the droplet at the opening of the cannula 42. In the case of unfavorable a angles the gold particles concentrate primarily in the first droplet (a too small) or in the last droplet (a too large) of a series. The optimum angle depends on the particle size and on the viscosity of the solution and must be determined empirically.

An essential element of the apparatus is the check valve 43 in the cannula 42 (or in a line leading to it). It consists of a quartz valve seat and a sapphire valve ball and is preferably oriented in the vertical direction. The check valve 43 is filled, as are the other parts of the metering device 4, with liquid paraffin (Grade 7174 of the MERCK Co., Darmstadt, Federal Republic of Germany) without air bubbles.

The metering aggregate 45–49 may be of any configuration, as long as it is capable of pumping over a maximum period of time of about 20 s, a volume of about 1 $\mu$l to a maximum of 10 $\mu$l. In a practical configuration, a volume of 1 $\mu$l to a maximum of 4 $\mu$l is metered in pumping steps of about 1 nl to about 50 nl. Preferably, a 3-way valve is provided, whereby a 1 ml syringe may be actuated, so that the paraffin may be refilled comfortably and the volume adjusted.

The suspension containing the gold particles is filled into the cannula 42. (For this, the cannula is temporarily removed from the pressure chamber 1). The suspension is conveyed indirectly by displacement by the metered liquid paraffin pumped in. The fill volume of the cannula 42 with suspension amounts for example to approximately 3–4 $\mu$l.

The atomizing effect, i.e. the size of the fog droplets, depends on the magnitude of the pressure impact in the pressure chamber 1. This size of the pressure impact also determines the gas velocity in the restriction and thus the particle velocity and its pulse. The pressure impact may be between 2–10,000 bar, for example between a few tens of bars and a few hundreds of bars, in particular a value of about 50 bar.

The particle size has a linear effect by means of the mass on the pulse of the particles. Fundamentally, small particles are more favorable for the survival of the cells impacted. On the other hand, large particles are more able to penetrate the cells. The optimum particle size must therefore be determined experimentally for each type of cell. Practical particle sizes are between 20 nm to 5 μm, in particular about 1–2 μm, specifically about 1.2–1.5 μm.

The material of the particles is in itself secondary. However, a high specific density and great inertia in chemical reactions (inert material) are favorable. It is further favorable when the particles are within the narrow size distribution, i.e. all of the particles are essentially of the same size. It is further advantageous in actual practice to use particles that may be produced in a simple manner, with good reproducibility within a narrow tolerance range in a wide range of sizes. Preferably therefore, gold is used as the material for the particles. Gold particles of uniform size may be produced from tetrachlorauric acid by reduction with photographic developers in a well reproducible manner. By diluting the initial solutions, particles with diameters between 5 μm down to the colloidal range (diameters smaller than 5 μm) may be produced. The arrest of the developing process with a fixative is critical for well reproducible gold particle sizes and for easily water soluble reaction products, which must be removed by centrifugation and washing with water. The finished gold suspensions are autoclaved.

A relatively critical value is the particle density in the suspension. Clogging suspensions cannot be used. Strongly diluted suspensions yield to many empty droplets and not enough hits in the cells. There is an optimum in between that must be determined for the corresponding cell types. The objective is to impact the highest number of cells with one particle only, as more particles drastically reduce the chances of survival of the cells. A practical value is around $10^{10}$ particles/ml.

The suspension volume possible per "shot", i.e. the volume of the droplets provided, should be as high as possible. However, if the suspension volume provided per shot is too high, the liquid accumulates in the restriction and a closed liquid filament will exit, which severely injures the cells. A practical value with internal diameters of the restriction around 100 μm is a droplet value of about 0.2 μl. A value of 0.5 μl was found to be too high in this case. In general, droplet volumes between 10 nl and 500 nl may be used. A droplet volume of between 50 nl and 150 nl is especially preferred.

The DNA concentration in the suspension may be chosen over a wide range between saturation and extreme dilution. For pBI221 and pHP23 plasmids for example values around 0.3 μg/μl are suitable. The plasmids may be present in a linearized or "supercoiled" form. In principle, a higher transformation rate may be expected from a higher DNA concentration.

If a restriction in the form of a diaphragm is used, the size of the fog droplets has a minimum for a suspension droplet volume of 0.2 μl at an internal diameter of the diaphragm of approximately 70 μm. Small droplets are essential in view of friction in flight and the braking effect of the particles upon impact, and the risk of injury at the point of impact. The latter is obviously also true for restriction in the form of a capillary. The size of the fog droplets also depends on the volume of the suspension droplets and may be affected by it.

The DNA to be introduced into the cells is usually freely dissolved in the liquid phase of the suspension. However, in certain cases it may be advantageous to modify the mounting of the plasmids on the gold particles for example by means of spermin or lactoferin.

The size of the target area, i.e. the area within which more than 80% of the particles are impacting, depends on the size and nature of the restriction (internal diameter, length of capillary, etc.), the working distance b and the vacuum. With a capillary with an internal diameter of 300 μm and a length of 10 mm, a working distance of 10 mm and the aforementioned water jet pump vacuum, an extremely small target diameter of maximum 0.7 mm may be obtained. The effective area within which the cells are impacted and the gold particles penetrate the cells is even smaller. It also depends on the cohesion of the cell walls. The particle density on the target area is a function of the working distance, the vacuum (scatter), the suspension density of the feed, the internal diameter of the restriction and the capillary length. The particle density on the target area should be adjusted so that as many cells as possible will be impacted by exactly one particle. The other parameters must be adjusted to this.

As during the bombardment of the cells a flow of gas exits from the restriction and impacts the cells, a secure mounting of them on the cell holder is essential. For example, 2% agarose on Thermanox (LAB-TEK Division, Yales Laboratories, Naperville Ill. 60540) may be used as the substrate. The agarose is poured in a thickness of 1 mm and contains 10 mM $CaCl_2$. The cells are bonded to the agarose with 4% alginate. The alginate hardens in the presence of $Ca^{2+}$ at room temperature. After about 1 h, polymerization is complete. Cells mounted in this manner are not blown away by the gas flow. This mounting process may be carried out readily in a sterile manner, is rapid and insures an adequate water supply of the cells until they are retransplated onto the medium.

The process according to the invention is carried out under sterile conditions. The gold particles, the DNA solution and all solutions and apparatus parts in contact with the cells are maintained sterile by autoclaving, sterile filtration or wiping or flushing with 70% ethanol. The entire apparatus is located under a sterile bench. The pressure chamber and the diaphragm or capillary are also flushed from time to time (1 to 2 times daily when in frequent use) with 70% ethanol. The suspension cannula is in addition occasionally autoclaved. In principle, no other sterility measures are required.

As mentioned above, the wall part 23 of the specimen chamber may be removed, together with the cell holder 25 and adjusting screws 27. In this manner the alignment of the cells to be bombarded relative to the reduction and the longitudinal axis (principal firing direction) is very simple. A test shot in 2% agar marks the target area. Subsequently, the wall part 23 of the specimen chamber is removed and mounted and oriented and positioned in a predetermined manner on a mechanical stage, under a stereomicroscope. The mechanical stage is now adjusted so that the target spot is centrally located in the graticule of the ocular lens. The cells can now be aligned by means of the two adjusting screws on the graticule and thus on the target area. The alignment may obviously also be carried out in a different manner.

The advantages of the process according to the invention and of the apparatus are obvious: a uniform distribution of individual particles on an extremely small target area is obtained. The particle density of on the target area and on the cells being bombarded, the pulse of the particles and the diameter of the target area may be finely controlled over a wide range. The DNA must not be coupled with or precipitated onto the particles, although this is possible. In addition the apparatus is very simple to operate and economical in its design.

The process described above for the preparation of transgenic plants is part of the present invention, together with all of its partial steps.

The process of the invention may be applied universally to cells of any plant, regardless of its taxonomic position. Especially suitable and thus preferred within the scope of the present invention is the use of cells in tissues, especially in tissues with few cells, but in particular meristematic tissues, such as those present for example in the budding meristema of plants, in proembryos and embryos or in embryogenic cell cultures. Obviously, however, any other suitable plant material may be used in the process of the invention, such as for example individual cells, zygotes, cell aggregates, plant organs, tissue, callus, etc.

The process of the present invention may also be applied to other eucaryontic cells such as, for example, animal cells or fungal cells, which may be isolated or part of a higher organized structure, algal cells, cells of single cell protozoa, etc.

The process of the present invention may also be applied to procaryontic cells such as bacterial cells or cells of cyanobacteria. Preferred are bacterial cells selected from the group consisting of enterobacterial cells, especially *E. coli* and Serratia cells, Agrobacterium cells, Bacillus cells, especially *Bacillus thuringiensis* and *Bacillus cereus* cells, Streptomyces cells, Pseudomonas cells, etc.

As the transforming DNA, both natural DNA sequences and hybrid gene structures produced artificially by means of recombinant DNA techniques may be applied.

The broad scope of the invention primarily covers recombinant DNA molecules, which contain DNA sequences leading to useful and desirable properties of the plant transformants.

These preferably are recombinant DNA molecules containing one or several gene sequences coding a useful and desirable property and subject to the regulatory control of expression signals active in the plants, so that an expression of said gene sequences in the plant cell transformed is assured.

For use in the process of the invention therefore primarily those genes are suitable, which are expressed in the plant cell and confer upon the plant a useful and/or desirable property, such as for example increased resistance to pathogens (for example against phytopathogenic fungi, bacteria, viruses, etc.), resistance to chemicals [for example herbicides (for example triazines, sulfonylurea, imidazolinones, triazolpyrimidines, bialaphos, glyphosates, etc.), insecticides or other biocides], resistance to harmful (endaphic or atmospheric) environmental effects (for example heat, cold, wind, in particular extreme soil characteristics, humidity, dryness, osmotic stress, etc.), or lead to the increased or improved formation of reserve or stored substances in leaves, seeds, tubers, roots, stems, etc. The desirable substances potentially produced by transgenic plants include for example proteins, starches, sugar, amino acids, alkaloids, scents, fats, etc.

Similarly, genes may be introduced by the process of the invention, which code pharmaceutically acceptable active substances, such as alkaloids, steroids, hormones, immunmodulators and other physiologically active substances.

Resistance against cytotoxins, for example, may be obtained by the transfer of a gene which codes an enzyme expressed in the plant cell, which detoxifies the cytotoxin, such as for example neomycinphosphotransferase Type II or aminoglycosid-phophotransferase Type IV, which contribute to the detoxification of kanamycin, hygromycin and other aminoglycosidantibiotics, or a glutathion-S-transferase, cytochrom P-450 or other catabolically effective enzymes, which are known to detoxify triazines, sulfonylureas and other herbicides. Resistance to cytotoxins can also be transferred by a gene, which expresses in the plant a certain form of a "target enzyme" (location of the attack by the cytotoxin), which is resistant against the activity of the cytotoxin, such as for example a variant of acetohydroxyacidsynthase, which is insensitive to the inhibiting action of sulfonylureas, imidazolinones or other herbicides interacting with this specific metabolic step; or a variant of EPSP synthase, which has been shown to be insensitive to the inhibiting action of glyphosates. It may be advantageous to express these modified target enzymes in a form making possible their transport into the correct cellular compartment, such as for example in the above case into the chloroplasts.

In certain cases, it may be of further advantage to direct the gene products into the mitochondria, the vacuola, the endoplasmatic reticulum or other cell regions, possibly even into the intercellular spaces (apoplasts).

Resistance against certain classes of fungi may be obtained for example by the introduction of a gene, that expresses chitinases in the plant tissues. Numerous plant pathogenic fungi contain chitin as an integral component of their hypha and spore structure, such as for example the basidiomycetes (smut and mildew fungi), ascomycetes and fungi imperfecti (including Altemaria and Bipolaris, *Exerophilum turcicum,* Colletotricum, Gleocercospora, Cercospora). Chitinase may be inhibited in the position of the pathogens determining mycel growth in vitro. A plant leaf or a root, which expresses chitinase constitutively or as a response to the infiltration of the pathogen, is protected against the attack of numerous different fungi. Depending on the situation, a constitutive expression may be advantageous compared to an inducible expression, which appears in many plants as a normal reaction to a pathogenic attack, as chitinase is present immediately in a high concentration, without having to await a lag phase for a new synthesis.

Resistance to insects may be transferred for example by a gene coding a polypeptide, which is toxic for insects and/or their larvae, such as for example the crystalline protein of Bacillus thuringiensis. A second class of proteins transferring resistance to proteins are the protease inhibitors. Protease inhibitors usually are a common component of vegetable storage structures. It has been shown that a Bowman-Birk protease inhibitor isolated from soy beans and purified, inhibits the intestine protease of Tenebrio larvae [Birk & al (1963)]. The gene coding the trypsinin inhibitor from cow peas is described by Hilder & al. (1987).

For use in the process according to the invention therefore primarily those genes are suitable, which lead to a protective effect in the transformed cells, the tissues developed from them particularly in the plants, such as for example an enhanced resistance to pathogens (for example phytopathogenic fungi, bacteria, viruses, etc.), to chemicals [for example herbicides (for example triazines, sulfonylureas, imidazolinones, triazolpyrimidines, bialaphos, glyphosates, etc.), insecticides and other biocides]; resistance to harmful (endophatic or atmospheric) environmental effects (for example heat, cold, wind, unfavorable soil conditions, humidity, dryness, etc.).

Genes used within the scope of the present invention may for example also include those leading to an increased formation of reserve or stored substances in leaves, seeds, tubers, roots, stems, etc. The desirable substances potentially produced by transgenic plants include for example proteins, starches, sugar, amino acids, alkaloids, flavines, scents, colorants, fats, etc.

Similarly, genes may be introduced by the process of the invention, which code pharmaceutically acceptable active substances, such as alkaloids, steroids, hormones, immunmodulators and other physiologically active substances.

The genes that may be considered within the scope of the present invention thus include known genes, but without being restricted to them, for example plant specific genes, such as the zein gene from corn, the avenin gene from oats, the glutelin gene from rice, mammal specific genes such as the insulin gene, the somatostatin gene, the interleucin gene, the t-PA gene, etc. or genes of a microbial origin, such as the NPT II gene, etc., together with synthetic genes, such as the insulin gene, etc.

In addition to naturally occurring structural genes, which code a useful and desirable property, genes modified in a specific manner by chemical or genetic engineering methods may also be used in the invention.

Furthermore, the broad concept of the invention also comprises genes entirely prepared by chemical synthesis. As genes or DNA sequences suitable for use within the present invention therefore both homologous and heterologous genes or DNA may be employed, together with synthetic genes or DNA. As example of a synthetic gene, the insulin gene is mentioned.

Within the scope of the present invention further the so-called "anti-sense" DNA may also be used; they lead in an operable combination with expression signals active in plant cells to the production of a RNA molecule, which is complementary to at least part of a mRNA coded by a "sense" DNA and is therefore capable of binding it. In this manner, the translation of a certain mRNA into the corresponding protein may be inhibited or at least restricted, so that there now exists a procedure whereby the effective control of the gene expression of selected genes in a plant is possible.

The DNA sequences usable in the present invention may be constructed exclusively from genomic cDNA or synthetic DNA. Another possibility is the construction of a hybrid DNA sequence consisting of both cDNA and also a genomic DNA and/or synthetic DNA.

In this case the cDNA may originate from the same gene as the genomic DNA, or both the cDNA and the genomic DNA may originate from different genes. In both cases, however, both the genomic DNA and/or the cDNA, each in itself, may be prepared from the same or from different genes.

If the DNA sequence contains portions of more than one gene, said genes may originate from one and the same organism, from several organisms belonging to different strains or varieties of the same type or to different species of the same genus, or from organisms belonging to more then one genus of the same or another taxonomic unit (kingdom).

In order to ensure the expression of said structural genes in the plant cell, it is advantageous if the coding gene sequences are first linked in an operable manner with expression sequences capable of functioning in plant cells.

Every promoter and every terminator capable of effecting an induction of the expression of a coding DNA sequence (structural gene), may be used as a constituent of the hybrid gene sequence. Especially suitable are expression signals originating from genes of plants or plant viruses. Examples of suitable promoters and terminators are those of the cauliflower mosaic virus gene (CaMV) or homologous DNA sequences, which still exhibit the characteristic properties of said expression signals. Bacterial expression signals are also suitable, in particular the expression signals of the nopaline-synthase gene (nos) or of the octopin-synthase gene (ocs) from the Ti plasmids of Agrobacterium tumefaciens.

Preferred in this invention are the 35S and 19S expression signals of the CaMV genome or their homologs, isolated by means of molecular biological methods, such as those described for example by Maniatis & al. (1982), from said genes and linked to the coding DNA sequence.

Homologs of the 35S and 19S expression signals are defined within the present expression as sequences, which in spite of slight sequence differences, are essentially homologous to the initial sequences and perform the same functions.

According to the invention the starting material for the 35S transcription control sequences, for example the ScaI fragment of the CaMV strain "S", which includes the nucleotides 6808–7632 of the gene card [Frank G. & al (1980)], may be used.

The 19S promoter and 5' not-translated region is located on a genome fragment between the PstI (Position 5386) and the HindIII position (Position 5850) of the CaMV gene card [Hohn & al (1982)). The corresponding terminator and 3' not translated region is located on an EcoRV/BgIII fragment between Position 7342 and 7643 of the CaMV genome.

Further preferred in the present invention are the expression signals of the CaMV strain CM 1841, the complete nucleotide sequence of which is described by Gardner & al. (1981).

Another effective representative of a plant promoter that may be used, is an overproducing plant promoter. This type of promoter should, to the extent that it is linked in an operable manner with the gene sequence coding the gene product desired, be able to transfer the expression of said gene sequence.

Overproducing plant promoters, which are used within the present invention, include the promoter of the small subunit (ss) of the ribulose-1,5-bisphosphate-carboxylase from soybeans, together with the promoter of the chlorophyll-a/b-binding protein. These two promoters are known for their property that they are induced in eucaryontic plant cells by light [see for example Genetic Engineering of Plants, an Agricultural Perspective, Cashmore, A. (1983)].

Additional regulatory DNA sequences that may be used for the construction of chimaeric genes comprise, for example, sequences capable of regulating the transcription of an associated DNA sequence in plant tissue in the sense of an induction or repression.

There are for example individual plant genes of which it is known that they are induced by different internal and external factors, such as plant hormones, heat shock, chemicals, pathogens, lack of oxygen, light, etc.

As an example of the regulation of genes by a plant hormone, mention should be made of abscisic acid (ABS) which is known to induce the excess in mRNAs in cotton during the late embryonal phase. Another example is gibberellic acid (GA3), which induces malat synthase transcripts in castor beans and in the aleuron layers of barley, isoenzymes of α-amylase.

The activity of glucanase and chitinase in bean leaves can be increased appreciably by treatment with the stress hormone ethylene. For chitinase, this induction effect is controlled by means of the promoter of the chitinase gene, which has been shown by reporter experiments using a promoter from the chitinase gene of beans (*Phaseolus vulgaris*).

The regulation of heat shock sensitive protein genes of soybeans has been investigated in detail. A treatment for several hours of the plants at 40° C. resulted in the de novo synthesis of so-called heat shock proteins. Numerous genes were isolated in the meantime and their regulation analyzed in detail. The expression of these genes are controlled primarily at the transcription level. If, for example, the promoter of the hps70 gene is fused with the neomycin-phosphotransferase II (NPT II) gene, the chimeral gene obtained in this manner may be induced by a heat shock (Spena & al., 1985). Another class of genes that may be induced in plants contains the light regulating genes, in particular the nuclear coded gene of the small subunit of ribulose-1,5-bisphosphatecarboxylase (RUBISCO). Morelli & al (1985) have shown that the 5' flanking sequence of a RUBISCO gene from peas is capable of transferring light inducibility to a reporter gene, if it is combined in a chimeric form with said sequence. This observation was extended to other light induced genes, such as for example the chlorophyll a/b binding protein.

The alcohol dehydrogenase genes (adh-gene) of corn were the object of intensive investigations. The adhl-s gene was isolated from corn and it was shown that a part of the 5' flanking DNA is capable of inducing the expression of a chimeric reporter gene (for example chloramphenicol acetyl transferase; CAT), if the temporarily transformed tissue was exposed to anaerobic conditions [Howard & al (1987)].

Another group of DNA sequences that may be regulated concerns chemically regulated sequences, which are present for example in the PR ("pathogenesis related proteins") protein genes of tobacco and may be induced by means of chemical regulators.

The regulable DNA sequences cited above as examples may be both of natural or synthetic origin or may consist of a mixture of natural and synthetic DNA sequences.

The various sequence sections may be linked to one another means of methods known per seto form complete DNA sequence expressible in plant cells. Suitable methods include for example the in vivo recombination of DNA sequences having homologous sections, and the in vitro linking of restrictions fragments.

Hybrid gene construction may be amplified very rapidly and simply by splicing into a suitable cloning vector and subsequent transformation of an appropriate host cell.

As cloning vectors, generally plasmid or virus (bacteriophage) vectors with replication and control sequences originating in species that are compatible with the host cell, are used.

The cloning vector usually carries a replication origin and specific genes leading to phenotypical selection characteristics in the transformed host cell, in particular to resistance to antibiotica or certain herbicides. The transformed vectors may be selected by means of these phenotypical markers after a transformation in a host cell.

Selectable phenotypical markers that may be used within the present invention include for example resistance against ampicillin, tetracycline, hygromycin, kanamycin, methotrexate, G418 and neomycin, without limiting the object of the invention.

As host cells within the invention prokaryonts may be used, including bacterial hosts, such as for example *A. tumefaciens, E. coli, S. typhimurium* and *Serratia marcescens*, together with cyanobacteria. Eukaryontic hosts, such as yeasts, mycel forming fungi and plant cells may also be used in the invention. The hybrid gene construction is spliced into a suitable cloning vector by means of standard methods, such as described for example by Maniatis & al (1982).

In the process, the vector and the DNA sequence to be spliced in is initially cut by means of suitable restriction enzymes. Suitable restriction enzymes are for example those which yield fragments with blunt ends, such as for example SmaI, HpaI and EcoRV, or else enzymes which form cohesive ends, for example EcoRI, SacI and BamHI.

Both fragments with blunt ends and those with cohesive ends that are complementary relative to each other, may be linked again using suitable DNA ligases in form of a continuous uniform DNA molecule.

Blunt ends may also be produced by treating DNA fragments with overhanging cohesive ends with the Klenow fragment of *E. coli* DNA polymerase by filling the gaps with the corresponding complementary nucleotides.

Cohesive ends, on the other hand, may be prepared artificially, for example by the attachment of complementary homopolymer tails to the ends of a DNA sequence desired and the cut vector molecule, using a terminal deoxynucleotidyl transferase or by the addition of synthetic oligonucleotid sequences (linker), carrying a restriction cleavage site and subsequent cutting with the corresponding enzyme. The cloning vector and the host cell transformed by the vector are usually employed to increase the copy number of the vector. With a higher copy number it is possible to isolate the vector carrying the hybrid gene construction and prepare it for example for the introduction of the chimeric gene sequence into the plant cell.

In a further process step these plasmids are used to insert the structural gene coding for the gene product desired or the non-coding DNA sequences with a regulatory function, for example an "anti-sense" DNA, into the plant cell and, optionally, to integrate it into the plant genome.

Another object of the present invention therefore concerns the preparation of recipient cells of plants containing the said structural genes or other desirable genes or gene fragments or other useful DNA sequences incorporated into their genome.

The broad concept of the invention thus also covers transgenic plants, in particular transgenic fertile plants transformed by means of the aforedescribed process of the invention and their asexual and/or sexual progeny, which still display the new and desirable property or properties due to the transformation of the mother plant.

The expression "asexual or sexual progeny of transgenic plants" therefore includes by definition according to the invention all mutants and variants obtainable by means of known processes, such as for example cell fusion or mutant selection and which still exhibit the characteristic properties of the initial transformed plant, together with all crossing and fusion products of the transformed plant material.

Another object of the invention concerns the proliferation material of transgenic plants.

The proliferation material of transgenic plants is defined relative to the invention as any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants.

Parts of plants, such as for example flowers, stems, fruits, leaves, roots originating in transgenic plants or their progeny previously transformed by means of the process of the invention and therefore consisting at least in part of transgenic cells, are also an object of the present invention.

The process according to the invention is suitable for the transformation of all plants, in particular those of the systematic groups Angiospermae and Gymnospermae. Among the Gymnospermae the plants of the class of the Coniferae are or particular interest.

Among the Angiospermae, in addition to the deciduous trees and bushes, plants of the families of the Solanaceae, Cruciferae, Compositae, Liliaceae, Vitaceae, Chenopodiaceae, Rutaceae, Alliaceae, Amaryllidaceae, Orchidaceae, Palmae, Bromeliaceae, Rubiaceae, Theaceae, Musaceae, Malvaceae or Gramineae and of the order of Leguminosae and here in particular those of the family of Papilionaceae, are of special interest. Preferred are representatives of the families of Solanaceae, Cruciferae and Gramineae.

The target cultures within the scope of the present invention include for example those selected from the series of: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Solanum, Petunia, Digitalis, Majorana, Cichorium, Helianthus, Lactuca, Bromus, Gossypium, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum, Ipomoeca, Passiflora, Cyclamen, Malus, Prunus, Rosa, Rubus, Populus, Santalum, Allium, Lilium, Narcissus, Ananas, Arachis, Phaseolus and Pisum.

Particularly suitable and thus preferred for the application of the process according to the invention are embryonal and/or meristematic structures, which may be present isolated or in the tissue of the entire plant. As a regeneration of entire plants beginning with embryonal and/or meristematic structures has, in the mean time, also become possible for numerous monocotyl plants, the following plants may also be used within the present invention: Lolium, Zea, Triticum, Sorghum, Saccharum, Bromus, Oryzae, Avena, Hordeum, Secale and Setaria.

Mature plants that have been raised from transformed plant cells, are crossed with themselves for the production of seeds. Some of the seeds contain the genes coding for the useful and desirable property, in a proportion exactly following the established laws of heredity. These seeds can be used for the production of transgenic plants.

Homozygotic lines may be obtained by repeated self-pollination and the production of inbred lines. These inbred lines may then be used to produce hybrids. In this process an inbred line containing the said foreign genes is crossed with another inbred line for production.

Following the general description of the present invention, reference is now made to specific examples to illustrate the invention without limitation, except where specifically indicated.

Non-limiting exemplary embodiments

1. PRODUCTION OF DNA/GOLD PARTICLE SUSPENSION 1.1 Plasmid

In the following transformation experiments Plasmid pBI221 is used, which expresses a β-glucuronidase enzyme. This plasmid may be obtained from CLONTECH, Palo Alto, Calif. and from GENOFIT, Geneva. Detailed data concerning its structure and composition are contained in a publication by Jefferson & al (1986).

In the transformation described in detail in the following Plasmid pBI221 is used in a "super-coiled" configuration in a concentration of approx. 1.25 μg DNA/μl $H_2O$. The DNA solution is stored at −20° C. and defrosted shortly before use.

1.2 Preparation of the gold particles

To 10 ml of an aqueous solution of 1% tetrachlorauric acid [$H(AuCl_2)\cdot 3H_2O$; Merck No. 1582] in an acutely tapering 15 ml plastic centrifugal tube, 200 μl of a photographic developer [for example "Rondial"], undiluted (AGFA) are rapidly (<10 s) added by pipette. The entire initial mixture is then briefly shaken. Following an incubation period of 30 s at room temperature the reduction reaction is arrested by the addition of 2 ml of a photographic fixer [for example "Ilfospeed", commercially available master solution, diluted 1+4 distilled $H_2O$; Ilford foto AG).

The suspension is then centrifuged 5 min at 2.2 k×g, [swing-out rotor, for example Vhrist Labofuge, HERAEUS) the excess discarded and the residue resuspended in 1.5 ml $H_2O$ and transferred into an Eppendorf vessel. The residual fixer salt is washed out by means of a second centrifugation (3 min at 10 k×g, Eppendorf centrifuge, fixed angle rotor). The residue is resuspended in 1.1 ml $H_2O$ and subsequently autoclaved in two aliquots at 1 bar and 120° C.

The autoclaved suspension contains $0.5(\pm 0.1)\times 10^9$ gold particles/ml. The mean particle diameter is 1.6±0.01 μm (standard error of the mean value), with a maximum particle diameter of 2.5 μm (one particle of approx. 50). The autoclaved suspension is stored in the refrigerator and resuspended shortly before use only.

1.3 DNA/gold Particle mixture

Immediately prior to use the following components are pipetted together:

3 μl pBI221 "supercoiled" DNA
6 μl gold suspension
1 μl 100 mM tris-HCl, pH 7.0
1 μl 1 mM Na-EDTA The control consists of a solution of the same composition, but containing instead of the pBI221 plasmid, water. In one of the experiments the gold suspension is diluted 1+9 with water.

2. PREPARATION OF THE PLANT MATERIAL TO BE TRANSFORMED 2.1 Corn embryos

The embryos are isolated shortly before maturity from the still unripe corn kernels and placed on a medium according to Murashige & Skoog (1962) [Table 1] in small Petri dishes.

2.2 Mounting of the corn embryos

2% agarose with 10 mM $CaCl_2$ are poured on small sterile Thermanox plates [22×60 mm, Miles Laboratories, Naperville, USA] so that a uniform, approx. 1 mm thick agarose layer is formed. The embryos are then mounted by means of a drop (<10 μl) 4% alginate [for example filter sterilized sodium alginate, Fluka No. 71238] on the agarose, wherein care must be taken that the scutellum is directed upwards. The alginate is hardened prior to the bombardment for 2–3 h in a humid chamber.

The embryos may be mounted in different manners. A process whereby the embryos are taken from the nutrient solution by means of a wire loop and adhesively bonded, following the removal of the excess liquid, with the aid of a filter paper, under a stereomicroscope onto the agarose substrate. The excess alginate is suctioned off with a sterile filter paper. Subsequently, the alginate is hardened for 2–3 h in a humid chamber. More than 40 embryos may be mounted on an agarose substrate adjacent to each other.

Immediately preceding the bombardment the agarose substrate is cut with a scalpel so that each of the embryos may be set individually, together with its agarose substrate, on a sterile microscope slide. The latter is then inserted into the specimen chamber in place of the device 23 of the apparatus described in detail above. By the application of a water jet pump vacuum the slide is suctioned onto the apparatus together with the embryo placed on it, but remains displaceable.

3. BOMBARDING PROCESS

3.1 Targeting

A stationary graticule marks the extension of the shooting axis. By setting the graticule upon the opening and moving the slide, the embryo is brought into the axis.

3.2 Loading of the cannula

To load the cannula described in detail above, it is temporarily removed from the pressure chamber 1. The paraffin (MERCK No. 7174) acting as the displacement liquid in the metering aggregate 45–49 is driven forward until the meniscus appears at the opening of the cannula. A 1 $\mu$l drop of the ready solution is placed on it with the pipette and drawn into the cannula by means of the metering aggregate 45–49. The cannula holds 2 to 3 $\mu$l of the suspension. When the last drop placed as described above has disappeared entirely in the cannula, the suspension meniscus is moved forward until it is flat with the end of the cannula and the latter is then screwed into the pressure chamber 1.

3.3 Shooting the suspension containing the DNA/gold particles into the corn embryos For the shooting of the suspension containing the DNA and the gold particles into the corn embryos, the following parameters are set on the apparatus according to the invention:

evacuation of the specimen chamber 2 by means of a water jet pump (approx. 500 mbar), $CO_2$ pressure during shot: 57 bar at 20° C., duration of individual shot: 2 ms, working distance (opening 42a of the cannula 42 to the specimen): 10 mm capillary (17): glass capillary with a length of 10 mm and a diameter of 300 um angle $\alpha$ between the cannula and the vertical: 90° number of shots per embryo: 1 or 5 (Table 2), charge volume per embryo: 0.2 $\mu$l, mode: a) 1 shot: 0.2 $\mu$l suspension (=charge)→1 shot b) 5 shots: 0.1 $\mu$l suspension (=charge)→2 shots 0.1 $\mu$l suspension (=charge)→3 shots

4. CULTIVATION OF THE EMBRYOS TRANSFORMED

Following the bombardment with the suspension containing the DNA and the particles, the embryo is taken from the alginate and cultivated in a medium according to Murashige & Skoog (Table 1). In the process, 5 to 7 embryos are set on 0.5 ml medium in recesses of tissue culture plates (with cover) [Costar plates with 24 recesses (diameter 16 nun); COSTAR, Cambridge, USA]. Advantageously, embryos are placed in the inner recesses only, while the outer ones are filled with 1 ml water each, so that the entire system serves as a humid chamber. The embryos are cultivated for 48 h at room temperature and day light [supplemented by artificial light: OSRAM L 36 W/77 Fluora at a distance of 15 cm).

5. GUS ($\beta$-GLUCURONIDASE) DETECTION

The transient expression of the O-gucuronidase gene is detected by a modification of the process described by Mendel & al (1989).

Reaction solutions:

Solution (a):

| Individual Components | Master Solution | Volume | Final Concentration |
|---|---|---|---|
| K/Na phosphate phosphate buffer (pH 7.0) | 0.5 M | 1000 $\mu$l | 0.1 M |
| Na-EDTA | 100 Mm | 500 $\mu$l | 10 mM |
| Triton-X | 1.0% | 500 $\mu$l | 0.1% |
| Potassium ferric Cyanide II | 50 mM | 500 $\mu$l | 5 mM |
| Potassium ferric Cyanide III | 50 mM | 500 $\mu$l | 5 mM |
| $H_2O$ | | 2000 $\mu$l | |

Solution (b):

Substrate solution consisting of: 5 mg 5-brom-4-chlor-indole-3-yl-$\beta$-D-glucoronic acid (Clontech Laboratories, Palo Alto USA) dissolved in 50 $\mu$l dimethylformamide. This substrate solution is always prepared freshly.

Solution (c):

Solutions (a) and (b) are mixed together and used immediately for GUS detection. In a deviation from Mendel & al (1989) this leads to a substrate concentration of 0.1%.

For GUS detection, initially the nutrient solution surrounding the embryos is removed with a pipette from the recesses of the tissue culture plates and replaced in each case with 0.5 ml solution (c) (sufficient for 5 to 7 embryos each). The closed culture plate is then incubated for 24 h at 37° C. in an incubator.

After 24 h, blue spots are seen on the embryos, indicating the presence of GUS activity in the embryonal cells. The spots are counted under a stereomicroscope. Table 2 lists the results of a representative experiment, with up to 14 spots being counted on positive embryos. Controls were negative without exception.

6. TRANSFORMATION OF BACTERIA

6.1 Transformation of *E. coli* cells

*Escherichia coli* cells of strain JM101 [Yanisch-Perron et al (1985)] are grown on a routine medium such as, for example, a LM-medium [Miller JH (1977)] over nitrocellulose filters. The filters are cut into squares of about 0.5 cm and layered on top of an equally sized piece of 2% agarose for shooting.

The probe is inserted into the specimen chamber as described in Example 2.2. For shooting of the suspension containing the pUC18 plasmid [Vieira and Messing (1982)] DNA and the gold particles to the bacterial cells, the following parameters are set on the apparatus according to the invention and remain unchanged throughout the experiments:

evacuation of the specimen chamber 2 by means of a water jet pump (approx. 900 mbar), $CO_2$ pressure during shot: 55 bar at 20° C., duration of individual shot: 2 ms, working distance (opening 42a of the cannula 42 to the specimen): see table 1 capillary (17): glass capillary with a length of 10 mm and a diameter of 200 um angle $\alpha$ between the cannula and the vertical: 45° mode: shots are directed to 3 places on each filter square with 3 shots [20 nl of DNA/particle suspension per shot] to each place The concentration of the DNA and the particles in the suspension, the size of the particles and the working distance is changed during the experiments according to table 1.

After shooting, the samples are incubated for one hour in a liquid LM-medium in order to remove the bacteria from the filter. Thereafter the bacterial suspension is plated onto a solid LM-medium, which is supplemented with ampicillin [100 μg/ml] for selection and with 1.5% agar. After incubation for 24 hours, the colonies are counted (see table 1). A selection of the positive colonies are analysed for the plasmid content. Plasmid is isolated from the bacteria and run on a gel. The size of the DNA is determined in comparison to a molecular weight marker [BRL; Bethseda Research Laboratories Life Technolgies; # 5615 SA/SB] and a standard plasmid [pUC18 cut with BamHI; 2.7 kbp]. All of the tested positive colonies contained the correct plasmid pUC 18

Controls are shot with particles but without DNA or incubated in a surplus of DNA without shooting. The controls were entirely negative.

Since the diameter of the bacteria is smaller than the particle size, it is very unlikely that cells, which took up a particle, are able to survive. It is to be assumed, therefore, that in case of a transgenic event, the particles just scratched the cell walls and the membranes and allowed the plasmid to flow in through a small opening which was closed afterwards and that the gold particle was left outside.

The above described processes for cultivating *E.coli* and for isolating and characterizing *E. coli* plasmids are standard procedures that are well known to the man skilled in the art and that are described in detail in Maniatis et al (1982).

7. TABLES

TABLE 1

Hormone-free medium according to Murashige & Skoog (1962) [MSO-2 medium; pH 5.8]

| Individual components | Concentration [mg/l] |
|---|---|
| $CaCl_2 \times 2H_2O$ | 440 |
| $NH_4NO_3$ | 1650 |
| $KNO_3$ | 1900 |
| KI | 0.83 |
| $CoCl_2 \times 6H_2O$ | 0.025 |
| $KH_2PO_4$ | 170 |
| $H_3BO_3$ | 6.2 |
| $Na_2MoO_4 \times 2H_2O$ | 0.25 |
| $MgSO_4 \times 7H_2O$ | 370 |
| $MnSO_4 \times 4H_2O$ | 22.3 |
| $CuSO_4 \times 5H_2O$ | 0.025 |
| $ZnSO_4 \times 7H_2O$ | 8.6 |
| $FeSO_4 \times 7H_2O$ | 27.85 |
| $Na_2$ EDTA | 37.25 |
| Glycine | 2.0 |
| Inosite | 100 |
| Nicotinic acid | 0.5 |
| Pyridoxine HCl | 0.5 |
| Thiamine HCl | 0.1 |
| Saccharose | 20.000 |

TABLE 2

Results of the transformation experiments described in Examples 1 to 5

| | Number of embryos treated | Number of transformants | Transformation frequency [%] |
|---|---|---|---|
| pBI221 | | | |
| 1) | 15 | 1 | 6 |
| 2) | 18 | 9 | 50 |
| 3) | 23 | 5 | 22 |
| Controls | | | |
| 1) | 8 | 0 | 0 |
| 2) | 11 | 0 | 0 |
| 3) | 20 | 0 | 0 |

Table 2 lists three independent experiments:
1) In Experiment 1 the particle concentration in the suspension is about $0.3 \times 10^6$ part/μl
In this case only one shot was fired with a suspension volume of 0.2 μl.
2) In Experiment 2 the particle concentration in the suspension is about $0.3 \times 10^6$ part/μl.
A suspension volume of 2×0.1 μl is distributed over 5 shots.
3) In Experiment 3 the particle concentration in the suspension is about $0.3 \times 10^5$ part/μl.
A suspension volume of 2×0.1 μl is distributed over 5 shots.

TABLE 3

Results of the transformation experiments described in Examples 6 Table 3

| | Parameter | | | | | | Results | | |
|---|---|---|---|---|---|---|---|---|---|
| # | a | b | c | d | e | f | g | h | i |
| 13/1 | 7 | 63 | 0.5 | 1.0 | 1x | 10 | 0 | 0 | 0 |
| 13/2 | 9 | 72 | 1.5 | 1.5 | 10x | 7 | 6 | 50 | 2 |
| 13/3 | 18 | 162 | 5.0 | 1.5 | 10x | 3 | 42 | 83 | 11 | legend:
: number of experiment
a: number of filter squares (= samples, 9 shots each)
b: total number of shots of the experiment
c: concentration of the plasmid in the DNA-particle suspension, given in μg/μl.
d: particle diameter, given in μm
e: particle concentration, given as arbitrary grey-steps
f: working distance, given in mm distance from the tip of the restriction to the surface of the sample
g: number of positive colonies
h: % of samples which contained positive colonies
i: maximum number of positive colonies per sample.

REFERENCES
1. Birk et al, *Biochime Biophy,s. Acta,* 67: 326–238, 1963
2. Cashmore A, "Genetic Engineering of Plants, an Agricultural Perspective", Plenum, New York, 1983, Seite 29–38
3. Chilton M-D, *Scientific American,* 248: 50–59, 1983
4. Christon et al, *Plant Physiol.,* 87: 671–674, 1998
5. De La Pena et al, *Nature,* 325: 274–276, 1987
6. Frank G et al, *Cell,* 21: 285–294, 1980
7. Gardner R C et al, *Nucl. Acids Res.,* 9: 2871–2888, 1981
8. Grimsley N H et al, *Nature* 325: 177–179, 1987
9. Hernalsteens J P et al, *EMBO J.,* 3: 3039–3041, 1984
10. Hilder V A et al, *Nature,* 330: 160–163, 1987
11. Hohn T et al, "Molecular Biology of Plant Tumors", Academic Press, Seite 549–560, 1982
12. Hooykaas-Van-Slogteren et al, *Nature,* 311: 763–764, 1984

13. Howard et al, *Planta,* 170: 535, 1987
14. Jefferson et al, *Proc. Natl. Acad. Sci., USA,* 83: 8447–8451, 1986
15. Klein et al, *Proc. Natl. Acad. Sci., USA* 85: 4305–4309, 1988
16. Maniatis et al, Molecular Cloning, Cold Spring Harbor Laboratories, 1982
17. Mendel et al, *Theor. Appl. Genet.,* 78: 31–34, 1989
18. Miller J H, Experiments in Molecular Genetics, 1972, Cold Spring Harbor Laboratory, New York, 3rd ed., 1977, p. 433
19. Morelli et al, *Nature,* 315: 200, 1985
20. Morikawa H und Yamada Y, *Plant Cell Physiol.,* 26: 229–236, 1985
21. Murashige und Skoog, *Physiol. Plant.,* 15: 473, 1962
22. Nomura K und Komamine A, *Plant Sci.,* 44: 53–58, 1986
23. Paszkowski J et al, *EMBO J,* 3: 2717–2722, 1984
24. Potrykus I et al, "Direct Gene Transfer to Protoplasts: An Efficient and Generally Applicable Method for Stable Alterations of Plant Genoms" in: Freeling M (ed.), Plant Genetics, A. R. Liss Inc., New York, pp. 181–199, 1986
25. Spena et al, *EMBO J,* 4: 2736, 1985
26. Steinbiss H H und Stable P, *Protoplasma,* 116: 223–227, 1983
27. Vieira and Messing, *Gene* 19: 259–268, 1982
28. Yanisch-Perron et al, *Gene* 33: 103, 1985
29. EP-A 0 270 356

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Process for accelerating DNA at target cells, comprising the steps of:
   a) placing target cells on a holder within a specimen chamber;
   b) flow-connecting one end of an essentially longitudinal pressure chamber to said specimen chamber via a restriction;
   c) projecting a cannula into said pressure chamber, said cannula having an outlet which opens within said pressure chamber, said outlet opening, said restriction and said target cells on said holder being located essentially on a straight line;
   d) providing a DNA solution;
   e) suspending microprojectiles in said DNA solution;
   f) feeding a small volume of said DNA solution comprising suspended microprojectiles via said cannula into said pressure chamber so as to form a drop of said DNA solution comprising suspended microprojectiles at the outlet of said cannula;
   g) generating a pressure impact within said pressure chamber, said pressure impact having a principal direction of propagation collinear with said straight line;
   h) atomizing said drop of DNA solution comprising suspended microprojectiles by said pressure impact into a fog of droplets of said DNA solution comprising said microprojectiles;
   i) accelerating said fog of droplets comprising said microprojectiles by said pressure impact in a direction towards said target cells, with DNA of said DNA solution adhering to said microprojectiles and being dragged with said microprojectiles; and
   j) bombarding said target cells with a pulse of said fog of droplets so that said microprojectiles which drag said adhering DNA solution penetrate the target cells to enable the DNA to enter said target cells.

2. Process according to claim 1, wherein said microprojectiles are gold particles of micrometer size.

3. Process according to claim 1, wherein said microprojectiles are tungsten particles of micrometer size.

4. Process according to claim 1, further comprising the steps of:
   pressurizing the fog of droplets generated by the step of atomizing and directing the microprojectiles with the DNA adhering to them through said restriction toward the target cells, the restriction being a diaphragm or a capillary, for accelerating and focusing said fog of droplets.

5. Process according to claim 4, wherein the target cells are located in an at least partially evacuated specimen chamber during said step of bombarding.

6. Process according to claim 5, wherein gold particles of an essentially uniform size in a diameter range of 20 nm to 5 um, and preferably 1.2–1.5 um are used as the microprojectiles.

7. Process according to claim 5, wherein a volume of said drop is within a range of 10–500 nl, and preferably about 50–150 nl.

8. Process according to claim 5, wherein a distance between the drop and the restriction is within a range of about 5–20 mm so that no closed liquid filament enters the restriction.

9. Process according to claim 5, further comprising the step of:
   producing the drop at the outlet of the cannula said cannula being inclined relative to a vertical, wherein an angle of the cannula to the vertical is chosen as a function of microprojectile size and viscosity of the DNA solution comprising the suspended microprojectiles, a concentration of the suspended microprojectiles being essentially constant in successive drops.

10. Process according to claim 4, wherein the restriction is a diaphragm having a free flow passage diameter within a range of 20 to 1000 micrometers. preferably within the range of 70–300 micrometer.

11. Process according to claim 4, wherein the restriction is a capillary having an internal diameter within a range of 20–1000 micrometers, preferably within the range of 70–300 micrometers, and further having a length within a range of 0.1–20 millimeters, preferably within the range of 1.0–10 millimeters.

12. Process according claim 5, wherein the pressure impact is between 2–10000 bar, and preferably several tens of bars to several hundreds of bars.

13. Process according to claim 5, wherein a DNA concentration of said DNA solution is several tenths ug per ul.

14. Process according to claim 1, wherein said target cells form plant tissue.

15. Process according to claim 14, wherein said plant tissue is meristematic tissue which includes a plurality of cells.

16. Process for accelerating DNA at target cells which are bacterial cells, comprising the steps of:
   a) placing target cells on a holder within a specimen chamber;
   b) flow-connecting one end of an essentially longitudinal pressure chamber to said specimen chamber via a restriction;
   c) projecting a cannula into said pressure chamber, said cannula having an outlet which opens within said pressure chamber, said outlet opening, said restriction and said target cells on said holder being located essentially on a straight line;
   d) providing a DNA solution;
   e) suspending microprojectiles in said DNA solution;
   f) feeding a small volume of said DNA solution comprising suspended microprojectiles via said cannula into said pressure chamber so as to form a drop of said DNA solution comprising suspended microprojectiles at the outlet of said cannula;
   g) generating a pressure impact within said pressure chamber, said pressure impact having a principal direction of propagation collinear with said straight line;
   h) atomizing said drop of DNA solution comprising suspended microprojectiles by said pressure impact into a fog of droplets of said DNA solution comprising said microprojectiles;
   i) accelerating said fog of droplets comprising said microprojectiles by said pressure impact in a direction towards said target cells, with DNA of said DNA solution adhering to said microprojectiles and being dragged with said microprojectiles; and
   j) bombarding said target cells with a pulse of said fog of droplets so that said microprojectiles which drag said adhering DNA solution penetrate the target cells to enable the DNA to enter said target cells.

* * * * *